(12) United States Patent
Vezina (10) Patent No.: US 7,131,769 B2
(45) Date of Patent: Nov. 7, 2006

(54) STRETCHER WITH DEDICATED MULTI-FUNCTIONAL REMOVABLE FLOATING PATIENT SUPPORT PLATFORM

(75) Inventor: Jean A. Vezina, Montreal (CA)

(73) Assignee: OctoStop Inc., Laval (CA)

( * ) Notice: Subject to any disclaimer, the term of this patent is extended or adjusted under 35 U.S.C. 154(b) by 148 days.

(21) Appl. No.: 11/012,173

(22) Filed: Dec. 16, 2004

(65) Prior Publication Data

US 2006/0133580 A1    Jun. 22, 2006

(51) Int. Cl.
    *A61B 6/04* (2006.01)
(52) U.S. Cl. .......................... 378/209; 378/177; 5/601
(58) Field of Classification Search ............... 378/177, 378/179, 180, 208, 209; 5/600, 601, 610, 5/611
    See application file for complete search history.

(56) References Cited

U.S. PATENT DOCUMENTS

| | | | |
|---|---|---|---|
| 3,947,686 A | 3/1976 | Cooper et al. | |
| 4,037,871 A | 7/1977 | Bourgraf et al. | |
| 4,145,612 A | 3/1979 | Cooper | |
| 4,977,630 A | 12/1990 | Oswalt et al. | |
| 5,996,149 A * | 12/1999 | Heimbrock et al. | 5/601 |
| 6,266,831 B1 * | 7/2001 | Heimbrock | 5/601 |
| 6,782,571 B1 * | 8/2004 | Josephson et al. | 5/601 |

* cited by examiner

*Primary Examiner*—Edward J. Glick
*Assistant Examiner*—Jurie Yun
(74) *Attorney, Agent, or Firm*—Ogilvy Renault LLP; Guy J. Houle (57) ABSTRACT

A stretcher with a dedicated multi-functional removable floating patient support platform is described. The stretcher has a lower frame assembly and an upper frame assembly is vertically displaceable thereover in an adjustable manner. The patient support platform is a rigid rectangular platform having a substantial portion thereof constructed of radiolucent material. The patient support platform is supported on bearings and retained captive on a platform support structure, whereby to slide axially thereof. Restraining hingeable side frames are provided and permit the patient support platform to be displaced laterally on the bearings to permit the patient support platform to be transferred from the platform support structure laterally thereof, in an effortless support manner.

31 Claims, 11 Drawing Sheets

STRETCHER WITH DEDICATED MULTI-FUNCTIONAL REMOVABLE FLOATING PATIENT SUPPORT PLATFORM

TECHNICAL FIELD

The present invention relates to a stretcher with a dedicated multi-functional removable patient support platform which can be displaced axially on bearing means and in a captive manner and which may also be displaced and removed from an upper platform assembly, laterally thereof on the bearing means, and in an effortless support manner.

BACKGROUND ART

There are a multitude of different stretcher structures and some of these comprise a base structure having a patient carrier which is removable from the base structure whereby to transport a patient to another location or a bed. U.S. Pat. No. 4,037,871 describes such a structure. However, the carrier portion of the stretcher is not suitable for multi-purpose use such as to support a patient under diagnostic equipment or for surgical procedures. In other words, the patient must be removed from such carrier. Furthermore, the carrier is not constructed for use with other support structures, other than the ambulance cot as described in that patent. U.S. Pat. No. 4,977,630 also shows a patient-mover device which is strappable on a stretcher. Again, the device is so constructed that it does not have multi-functional uses, and the patient must be removed therefrom, and transferred to other support structures for diagnostic or surgical procedures. Many hospital beds or stretcher structures are known whereby to tilt a patient to a Trendelenberg position. The use of extendible cylinders to effect such displacement of the patient support structure is also known as can be seen from U.S. Pat. No. 4,912,787. This patent also teaches that the top or the patient-support portion of the stretcher can be used for x-ray examination. A patient-support platform for x-ray diagnostic purposes is known for example, from U.S. Pat. Nos. 3,947,686 and 4,145,612.

It is pointed out that known stretcher construction or hospital bed structures provide various features, but during the transport of a patient, it becomes necessary to transfer the patient from the stretcher structure in order to transfer the patient to diagnostic devices or for surgical procedures, and such displacement and transfer can be harmful to the patient. Accordingly, there is a need to provide a stretcher wherein the patient can be supported on a dedicated multi-functional support platform and undergo examinations, or interventional radiology, or surgical procedures until it becomes safe to transfer the patient onto a hospital bed.

SUMMARY OF INVENTION

It is a feature of the present invention to provide a stretcher with a dedicated multi-functional removable patient support platform which has multiple uses and which can support a patient thereon and which is removably secured to a stretcher frame assembly and easily removed therefrom in an effortless manner and which may be used for diagnostic, interventional radiology or surgical procedure on the patient, and further, wherein the patient may be inclined, such as at a Trendelenberg position on the stretcher frame assembly.

According to the above feature, for a broad aspect, the present invention provides a stretcher with a dedicated multi-functional removable patient support platform. The stretcher comprises a lower frame assembly supported on casters for displacing the stretcher on a support surface. An upper frame assembly is supported elevated from the lower frame assembly. Adjustable vertical supports adjustably interconnect the upper frame assembly to the lower frame assembly. Means is provided to extend and retract the vertical adjustable supports to adjust the height of the upper frame assembly relative to the lower frame assembly. The patient support platform is a rigid rectangular platform having a substantial portion thereof constructed of radiolucent and MR (magnetic resonance). compatible material. Detachable securement means is provided for removably securing the patient support platform to a platform support structure of the upper frame assembly The platform support structure has longitudinal axial restraining guide means to permit limited axial displacement of the patient support platform on the platform support structure. Intermediate bearing means is provided between the platform support structure and the patient support platform, to permit effortless limited longitudinal displacement of the patient support platform on the platform support structure. Detachable securement means is displaceable from an engaged position to a disengaged position, at which the patient support platform can be displaced laterally on the intermediate bearing means to permit the patient support platform to be transferred from the platform support structure laterally thereof, in an effortless support manner.

BRIEF DESCRIPTION OF DRAWINGS

A preferred embodiment of the present invention will now be described with reference to the accompanying drawings in which.

DESCRIPTION OF PREFERRED EMBODIMENTS

Figure 1:
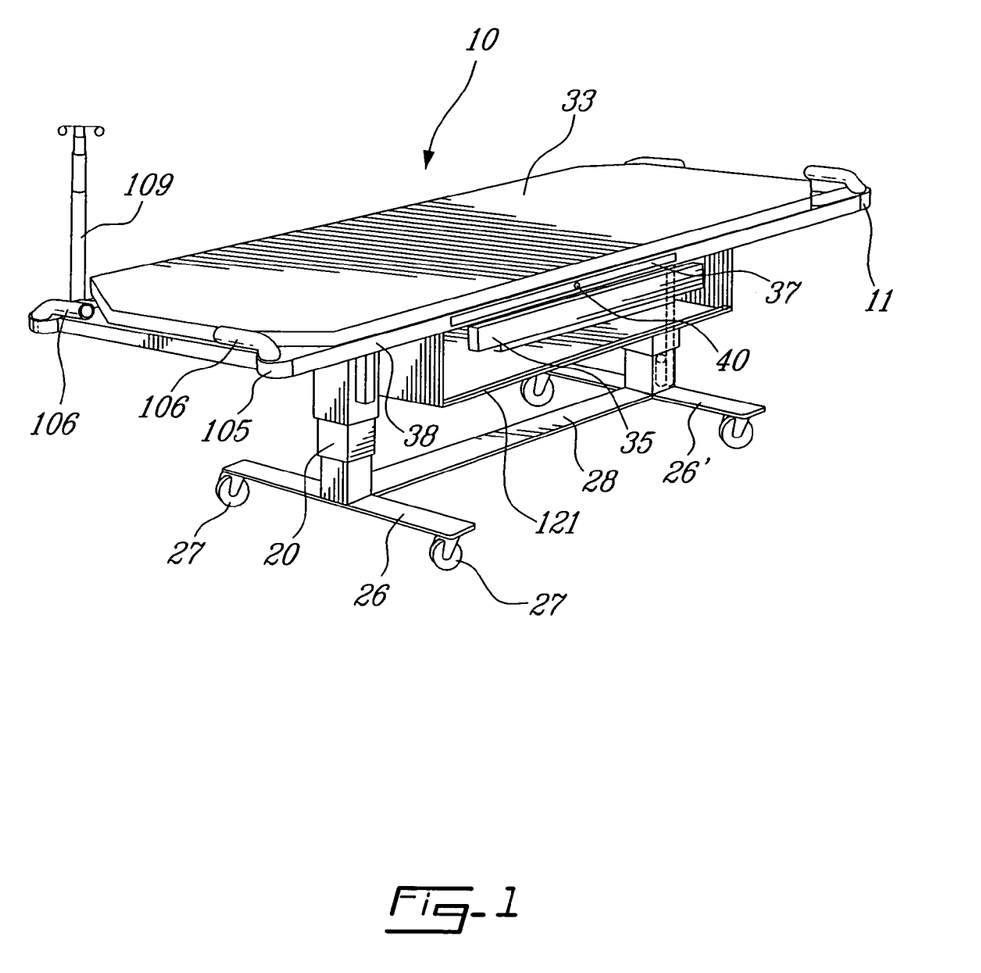
FIG. 1 is a perspective view of a stretcher constructed in accordance with the present invention illustrating the dedicated multi-functional removable patient support platform and some of its associated features.
Figure 2:
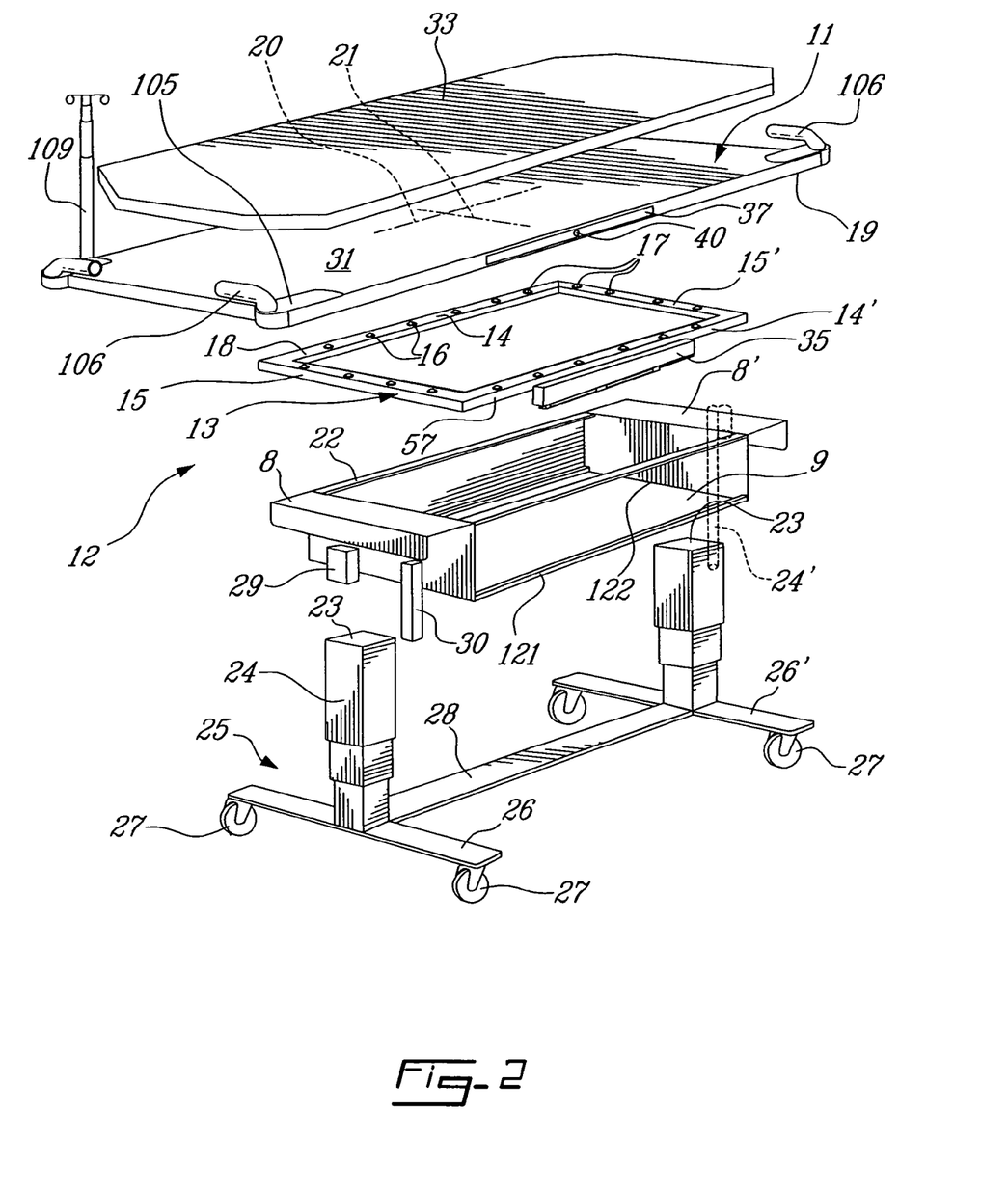
FIG. 2 is a perspective explosion view illustrating the construction of the stretcher of the present invention.
Figure 3:
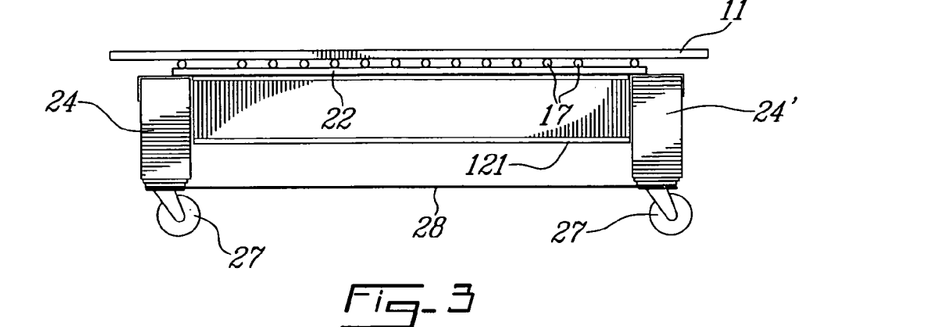
FIG. 3 is a side view showing the stretcher with the patient support platform at its lower-most position.

Referring now to the drawings and more particularly to FIGS. 1 to 3, there is shown generally at 10 a stretcher constructed in accordance with the present invention. It comprises a dedicated multi-functional removable patient support platform 11 removably secured to a platform support structure or frame 12, as can be seen in FIG. 2. The platform support structure 12 is comprised of a rectangular bearing support frame 13 defining opposed parallel arms 14 and 14' and transverse parallel end arms 15 and 15'. Bearing retaining cavities 16, are provided in a spaced-apart manner along these parallel arms, whereby to retain spherical bearings 17 therein and which project above the top surface 18 of the bearing support frame 13. Longitudinal rows and transverse rows of bearings are provided and on which a flat lower surface 19 of the patient support platform 11 rests, whereby to provide effortless floating displacement of the platform 11 in either axially along the longitudinal axis 20, or laterally along the lateral axis 21 as will be described later.

The upper frame assembly also comprises a lower rectangular support frame 22 forming an upper end of a rectangular casing 9 which is immovably secured to the upper end 23 of opposed adjustable supports by connecting flanges 8 and 8'. The adjustable supports are provided by a pair of telescoping cylinders 24 and 24' which are mounted on a lower frame assembly 25 which consists of transverse end frames 26 and 26' interconnected by a transverse beam 28. Casters 27 are connected to opposed ends of the end frame whereby to displace the stretcher 10 on a flat support surface. It is pointed out that the support platform 11 can be attached on top of an ambulance stretcher and then transferred at a hospital onto the support frame 12 and secured thereto, as will be described later. The cylinders 24 and 24' are driven in synchronism by an internal electrical motor (not shown) whereby to actuate an internal drive train assembly which may be a rack and pinion type assembly to extend or retract the cylinders 24 and 24', whereby to adjust the height of patient support platform 11. A battery 29 and control 30 is conveniently located to provide power and to control the cylinders.

Figure 4A:
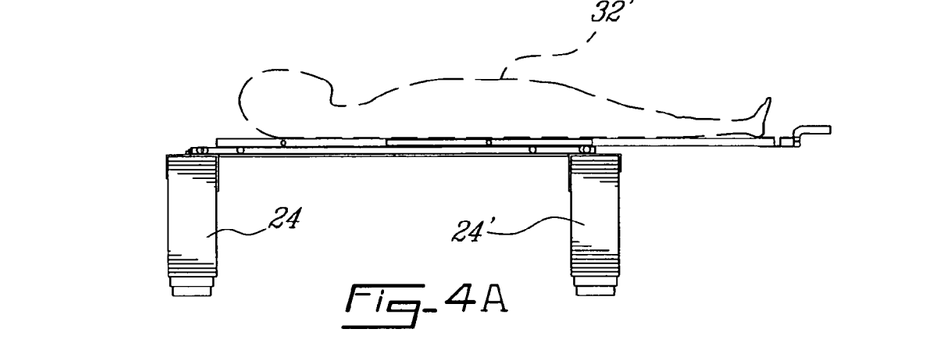
FIGS. 4A and 4B are side views showing the limited axial displacement of the patient support platform on the platform support structure.
Figure 4B:
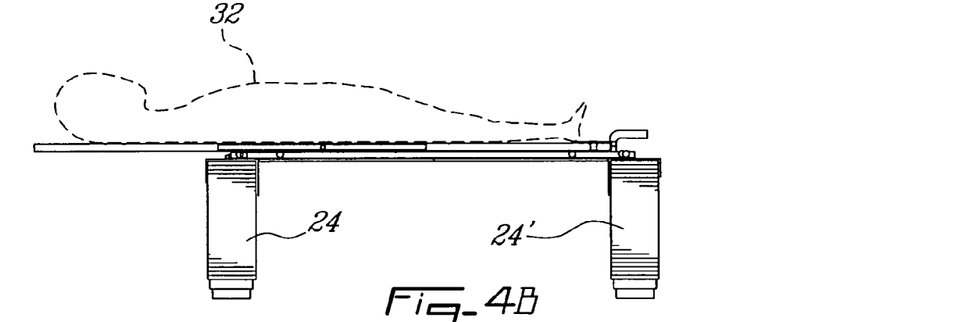
Figure 5:
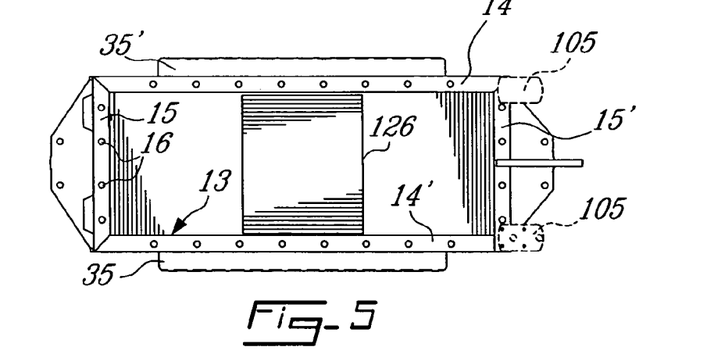
FIG. 5 is the top view showing the construction of the platform support structure under the patient support platform.
Figure 6:
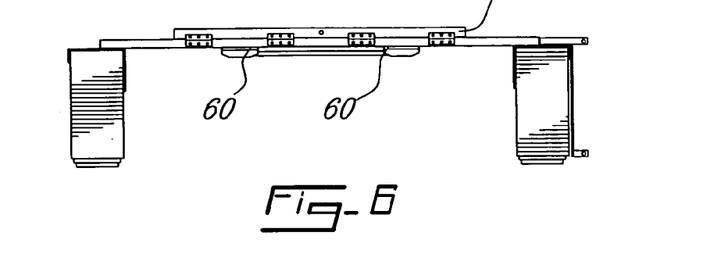
FIG. 6 is a side view of the platform support structure.

The patient support platform 11 is a rigid rectangular platform which has a substantial portion 31 thereof constructed of radiolucent material whereby a patient 32, as shown in FIGS. 4A and 4B, supported thereon or on the foam pad 33 can be transported to diagnostic equipment such as x-ray machines, MRI's and CT scanning machines for purpose of examination without moving the patient from the support platform 11, in a manner as will be described herein below. In order to do so, it is necessary that the patient support platform 11 be removed from the bearing support frame 13 of the upper platform support assembly 12.

Figure 9A:
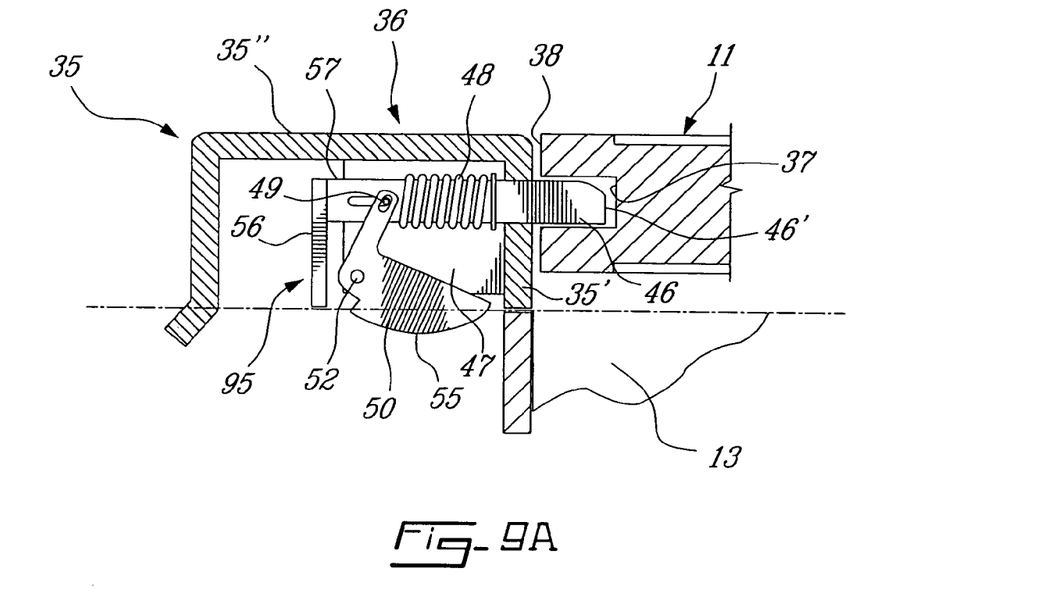
FIGS. 9A and 9B are simplified side views illustrating the construction of the plunger bolt assembly showing the hinge restraining side frames in an engage position, in FIG. 9A, and a disengaged position in FIG. 9B.
Figure 9B:
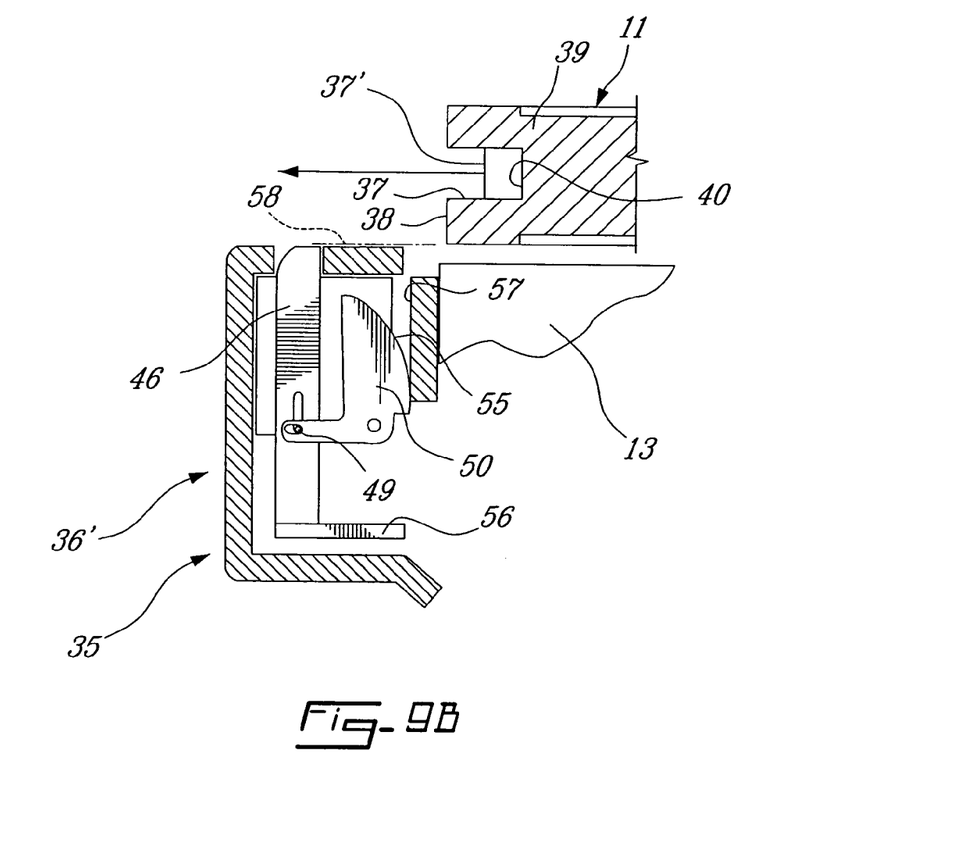
Figure 11:
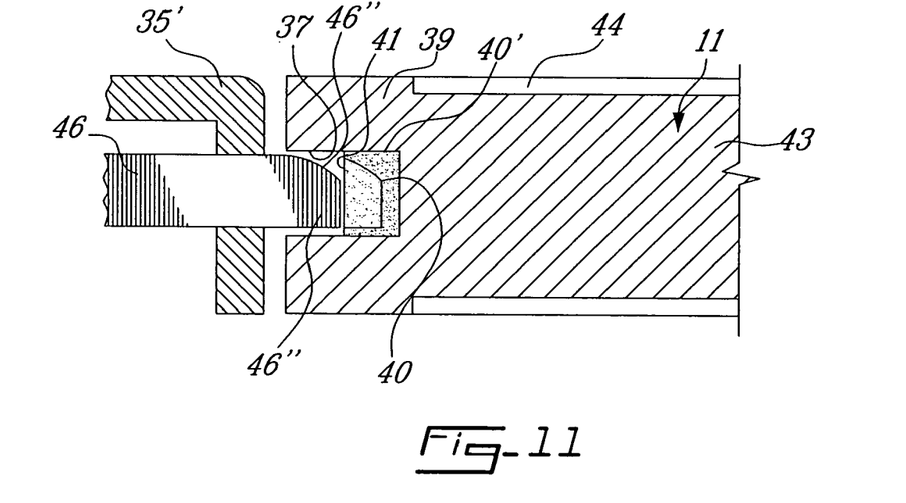
FIG. 11 is a section view showing the construction of an edge portion of the patient support platform illustrating the construction of the guide channels and the bolt head receiving cavity.

The detachable securement means for the patient support platform 11 is constituted by opposed restraining side frames 35 which are displaceable from an engaged position, as shown at 36 in FIG. 9A, to a disengage position 36', as shown in FIG. 9B. Referring now to FIGS. 9A, 9B and 11, there will be described the axial restraining guide means which permits limited axial displacement of the patient support platform 11 on the bearing support frame 13. As shown in FIGS. 9A, 9B and 11, guide channels 37 are provided along the side edge wall 38 of the patient support platform 11 and these channels, as shown in FIG. 1, are centrally located therealong and extend a predetermined length. These channels 37 are formed in a Delrin® plastics edge material 39, as shown in FIG. 9B, extending along opposed side edge walls 38 of the patient support platform. A central bolt head receiving cavity 40 is also bored centrally in an end wall 41 of the guide channels 37. As shown in FIG. 11, the remaining portion of the patient support platform 11 is of a radiolucent rigid foam material 43. The opposed surfaces also have a thin Kevlar® sheet 44 bonded thereto. Accordingly, the patient support platform is a very rigid light weight platform which is easily sanitized and which is radiolucent in a major portion thereof.

Figure 9C:
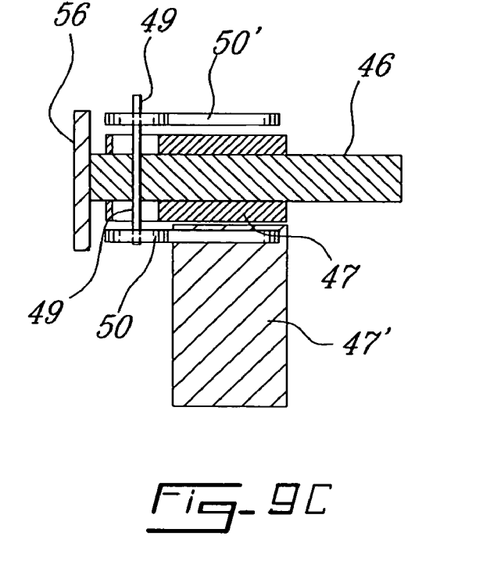
FIG. 9C is a top view of the plunger bolt assembly with the bolt in an engaged position.
Figure 9D:
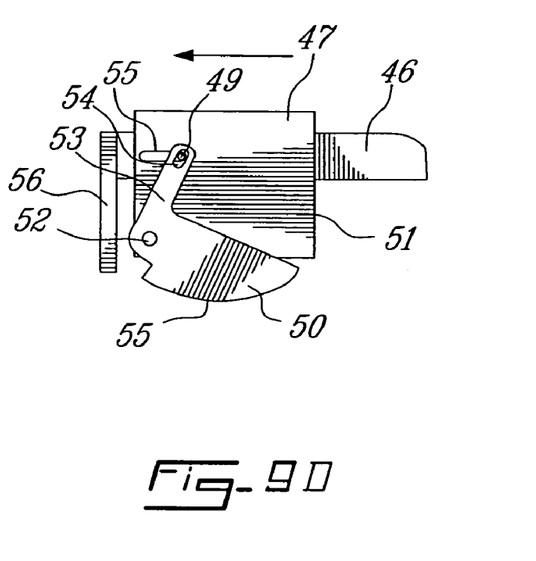
FIG. 9D is a side view showing the bolt having been retracted by the retracting flange secured thereto and illustrating the position of the retracting cam.

The longitudinal axial restraining guide means therefore comprises, in part, the opposing guide channels 47 and the restraining side frames 35 which carry a plunger bolt actuating mechanism 45 as will now be described with reference to FIGS. 9A to 9D. As herein shown, the plunger bolt actuating mechanism 45 comprises a plunger bolt 46 which is retained in a plunger bolt housing 47 and biased outwardly, as shown in FIG. 9A, by a biasing coil spring 48 retained within the housing. The housing 47 is immovably secured to the inner wall 35' and/or top wall 35" of the pivotal housing 35. A retracting pin 49 is secured transversely to the plunger bolt and extends on opposed sides of the housing 47, as shown in FIG. 9C. As herein shown and with further reference to FIG. 9D, a cam 50 is pivotally secured to the opposed side walls 51 of the housing 47 on pivots 52. Each cam 50 and 50' has a bolt retracting arm 53 which has a slot 54 in an end portion thereof, with the retracting pin 49 being captive in this slot. The side walls 51 of the housing are further provided with an axial longitudinal slot 55 to permit displacement of the pin 49 therealong when the bolt 46 is retracted.

As shown in FIGS. 9A to 9D, the cam 50 has a curved cam actuating edge 55, the purpose of which will be described later. A finger engaging retracting flange 56 is secured to a rear end 57 of the plunger bolt 46 to retract the bolt into the housing against the forwarding spring pressure of the coil spring 48 whereby to manually retracted the bolt to disengage the bolt head 46' from the bolt head receiving cavity 40, to disconnect the restraining side frame 35 from the patient's support platform 11 and to move the side frame to the disengage position shown at 36' in FIG. 9B. As shown in FIG. 9B, when the restraining side frame 35 is at its disengage position, the cam actuating edge 55 maintains the plunger bolt 46 in its retracted position with the plunger bolt edge maintaining the cam in its retracted position, as it is biased against the edge wall 57 of the bearing support frame 13. The weight of the restraining side frame 35 maintains it in the retracted position and overcomes the spring force of the coil spring 48. As shown in FIG. 9B, the retracted pin 49 is at the end of the slot. 55 provided in the side walls of the housing.

As herein shown also, the restraining side frame 35, when in a plunger bolt disengage position, is located below the horizontal plane 58 of the spherical bearings 17 to provide unobstructed lateral displacement of the patient support platform 11 on these bearing and laterally on the bearing support frame 13 to transfer the platform on another support table or to carry it away with the patient strapped or undisturbed thereon.

Figure 7A:
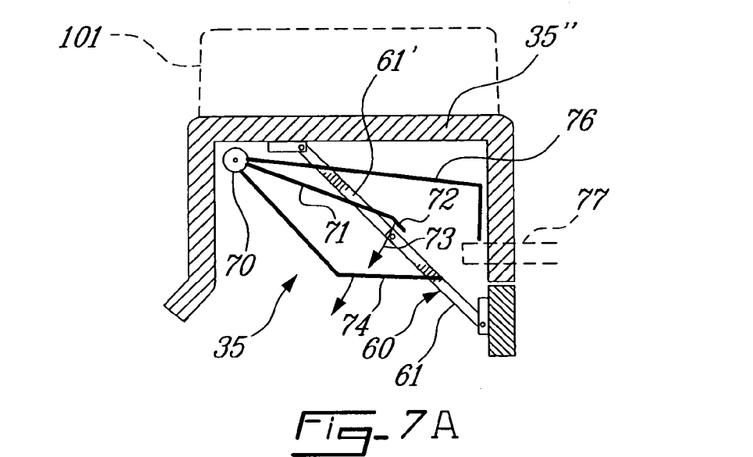
FIGS. 7A to 7C are simplified section views showing the hinge mechanism of the restraining side frames and the actuating and locking features thereof.
Figure 7B:
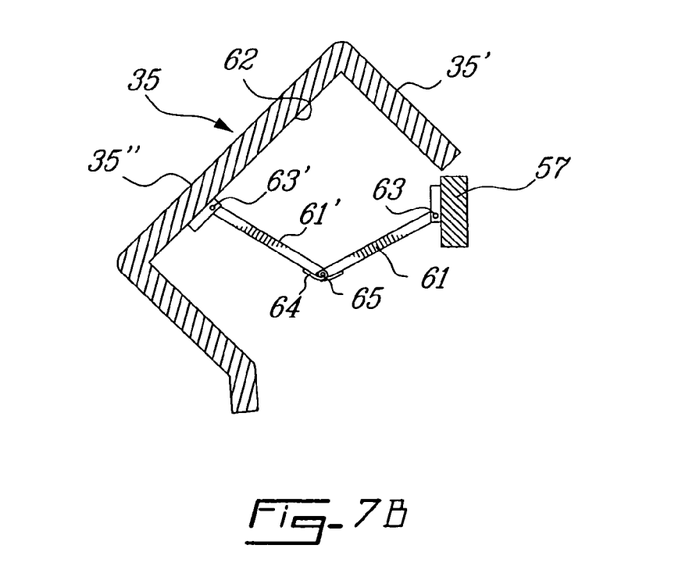
Figure 7C:
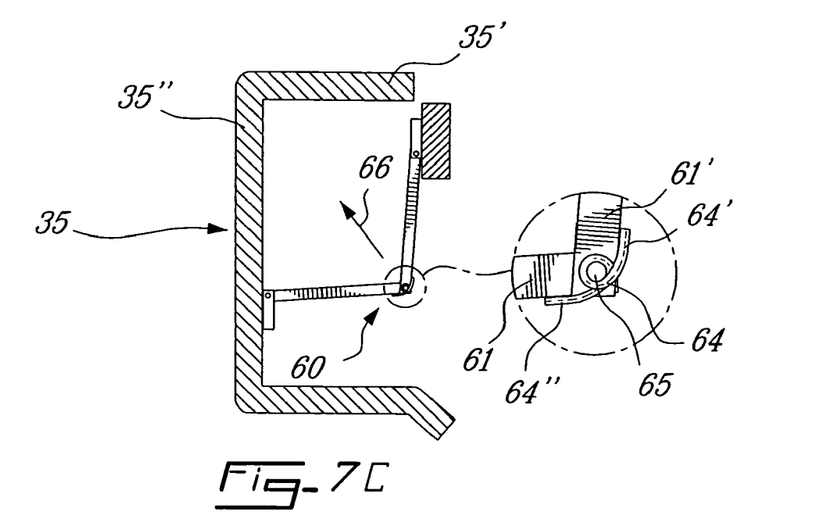

Referring now to FIGS. 7A to 7D, there will be described the construction of the hinge restraining side frames 35 and 35'. Only one of the side frames will be described as the other one is identical in construction. These side frames have an inverted U-shaped cross section as illustrated in FIGS. 7A to 7C, and are each provided with two spaced-apart spring bias hinge assembly 60. Each spring bias hinge assembly 60 comprises a two leaf hinge with one leaf 61 connected to the edge wall 57 of the bearing support frame 13 and the other leaf 61' connected to the underface 62 of the top wall 35" of the side frame 35. They are hingedly connected thereto on hinge pins 63 and 63' respectively. A biasing spring 64 is secured about a leaf interconnecting hinge pin 65. This is better illustrated in the exploded view of FIG. 7C. The biasing spring 64 has one spring end 64' biased against one of the leaf sections 61' and another end 64" biased in opposite direction against the other leaf section 61 whereby to apply a restoring force in the direction of arrow 66. However, the strength of the spring 64 is so selected, that the weight of the restraining side frame 35 overcomes this restoring force. When the restraining side frame is in its engaged position, as shown in FIG. 7A, the spring 64 will displace the adjacent ends of the spring leaves 61, 61' inwardly of their axial plane, thereby providing support leverage of the side frame at their engage position.

Figure 8:
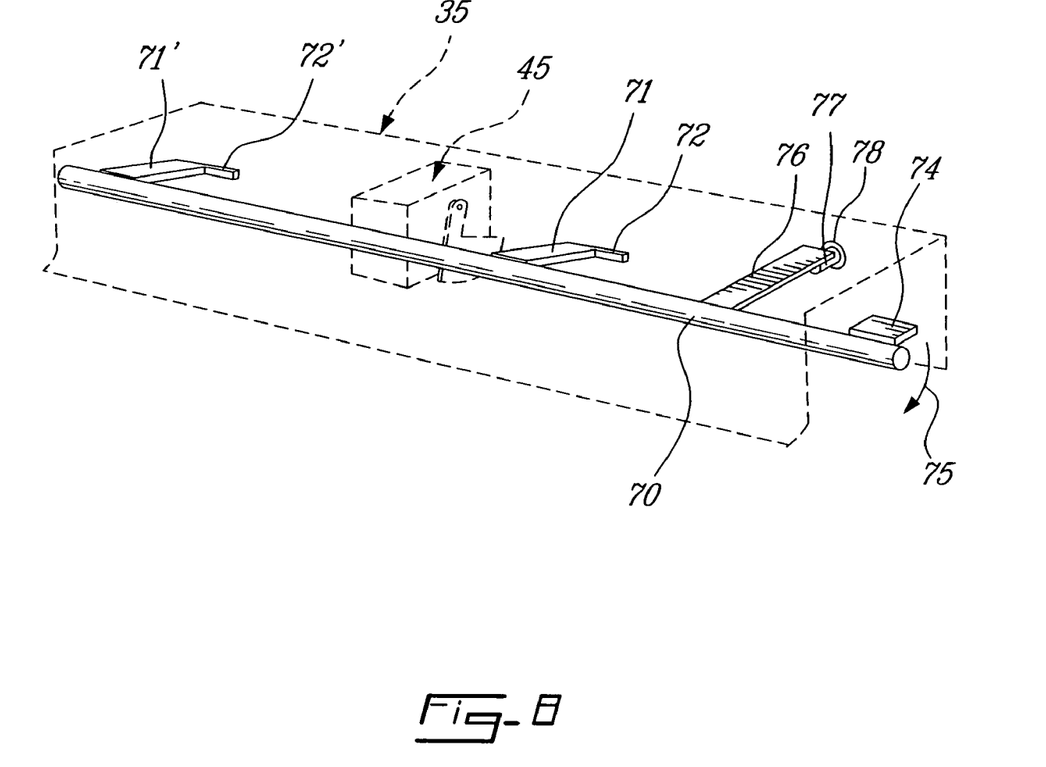
FIG. 8 is a perspective view of the actable pivotal rod which disengages the hinges of the restraining side frames.

In order to disengage the spring bias hinge assembly 60 there is provided, as shown in FIG. 8, a pivotal rod 70 which is retained under the U-shaped side frame 35 for longitudinal axial rotation thereof. As herein shown, the pivotal rod 70 is provided with a pair of hinge disengaging fingers 71 and 71' there being two of such fingers as there are two hinge assemblies 60 under each of the side frames 35 and 35'. These hinge disengaging fingers 71 are immovably secured to the pivotal rod 70 and have trip projections 72 and 72' which extend above the biasing spring 64 to apply a downward force, as illustrated by arrow 73, on the spring to trip the leaf sections 61 of the hinge. By tripping the hinge, the side frames hinge downward, after the plunger bolt 46 has been retracted by a user person, in the manner as previously described. FIG. 8 also illustrates the position of the plunger bolt actuating mechanism 45 which is centrally located along the restraining side frame 35. The pivotal rod 70 is actuated at a free end thereof, by a finger engaging leaver 74 which is accessible under the side frame 35 at one of its ends. As herein shown, by depressing the finger engaging lever 74 in a downward direction, as indicated by arrow 75, the pivotal rod axially rotates to disengage the hinges.

Figure 7D:
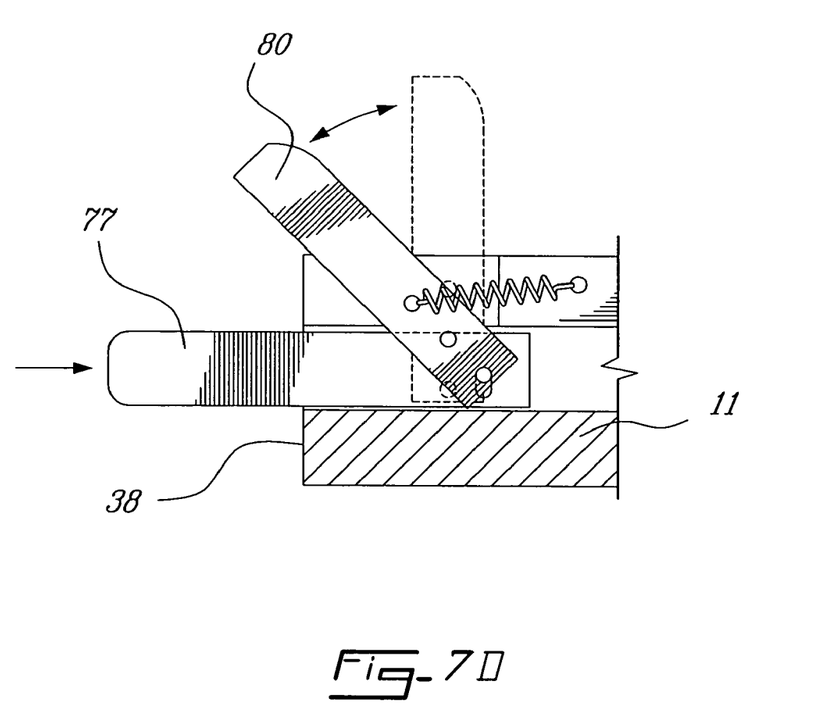
FIG. 7D is a simplified section view showing connectable locking element for preventing disengagement of the hinge structure.

As shown in FIG. 8, the pivotal rod 70 is provided with an arresting means in the form of a flange 76 immovably secured to the rod 70 and displaceable when the rod axially rotates. This flange engages an arresting pin 77 of a mechanical sensor 79 which projects in a hole 78 provided on the inner wall 35' of the side frame 35 when the sensor 79 is actuated, the pin 77 projects through the inner wall 35' and prevents the pivotal rod 70 from being axially rotated to trip the hinges which may accidentally disconnect the restraining side frames. This is a safety feature when the upper support frame assembly is pivoted to the Trendelenberg position, as illustrated in FIG. 12B. A spring biased sensor arm 80 actuates the pin 77, as shown in FIG. 7D, and this pin is automatically retracted as soon as the upper frame assembly is lowered to its horizontal position to depress the sensor arm 80.

Referring now to FIG. 11, there will be described the operation of the plunger bolt 46' engaged within the bolt head receiving cavity 40, or in the guide channel 37. When the plunger bolt 46 is engaged within the cavity 40, the patient support platform is locked centrally on the bearing support frame 13. The plunger bolt head 46' may have a sloped upper edge 46" and the cavity 40 may have a like slopped top inner wall portion 40' for sliding frictional engagement with the slopped upper edge 46" of the bolt whereby to provide downward clamping engagement. In order to axially displace the patient support platform, actually, to position the patient either in a forwardly projected position, as illustrated at 32' in FIG. 4A, or at a rearwardly projected position as shown at 32" in FIG. 4B, it is necessary to pull the plunger bolt rearwardly, by retracting the retracting flange 56, and to then displace the patient support platform whereby the bolt head 46' rests in the guide channel 37 and abuts against its inner wall 37' in sliding friction, as shown in FIG. 9B. For security purpose, two persons must simultaneously pull the plunger bolt of each side assembly. Accordingly, the patient support platform can now be displaced axially, and as previously described. These channels are of a predetermined length, whereby approximately 25% of the surface area of the patient support platform is projected from either end, maintaining a major portion of the weight of the patient between the support cylinders 24 and 24' or wheel supports.

Figure 10A:
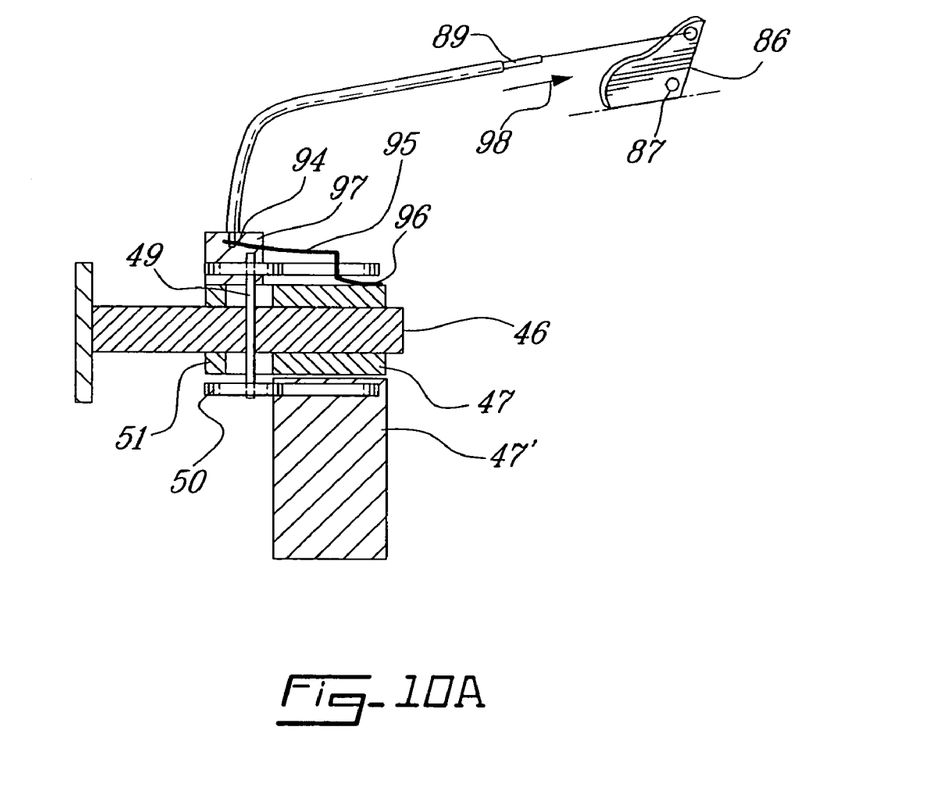
FIGS. 10A and 10B are simplified schematic views showing the construction of the bolt arresting mechanism, with FIG. 10A showing the bolt in an unlock position and FIG. 10B showing the bolt in a lock position.
Figure 10B:
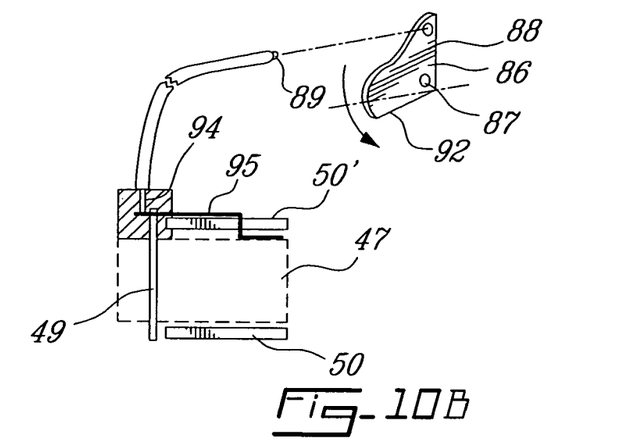
Figure 10C:
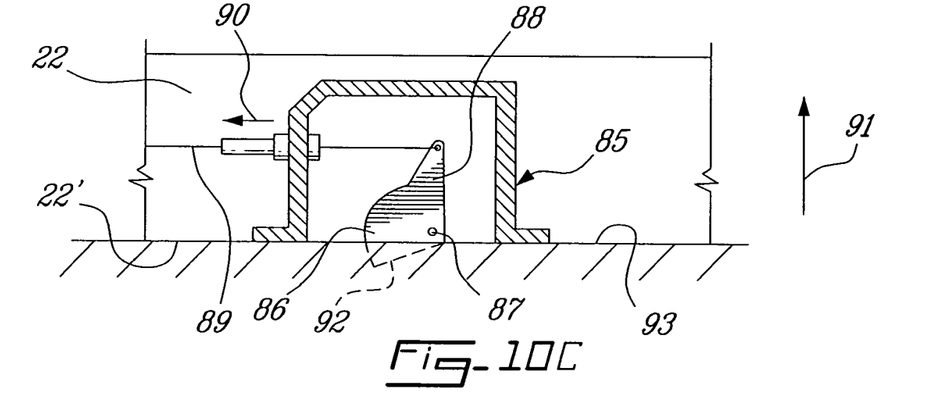
FIG. 10C is a simplified side view showing the construction of the actuator which automatically locks the plunger bolt when the platform support structure is hinged to an angular position.

With reference now to FIGS. 10A and 10B, there will be described the construction and operation of a plunger bolt arresting means to maintain the plunger bolt 46 extended from its housing 47 into the bolt head receiving cavity 40, to immovably secure the patient support platform 11 to the platform support structure 12. This bolt arresting means comprises an actuator 85, shown in FIG. 10C, which is secured in the bottom wall of the lower surface 22' of the lower rectangular support frame 22, at an elevating end 100 thereof, as shown in FIG. 12B. This actuator has a pivoting lever 86 mounted on a pivot pin 87, secured in the housing 85'. The pivoting lever 86 has a cable attaching arm 88 secured to a cable 89 which applies a pulling force in the direction of arrow 90 thereto. As soon as the rectangular support frame 22 is lifted in an upward direction, as shown by arrow 91, the pulling force of the wire 89 causes the pivoting lever to hinge outwardly of the actuating housing 85 to its position shown by phantom lines 92. This causes forward movement of the cable 89, in the direction of arrow 90, as the lower surface 22' of the support frame 22 has moved away from the lower bearing surface 93, which may be the upper end 23 of the cylinder 24'. As soon as the cable 89 moves forwardly, the bolt arresting means is engaged, preventing retraction of the bolt.

As shown in FIG. 10A, the cable 89 has its remote end 94 connected to a retracting pin arrester spring herein constituted by a leaf spring 95 constructed of spring steel material capable of retaining its shape and secured at one end 96 to a side wall of the housing 47 of the retracting bolt 46. The spring 95 has a hole 97 disposed aligned with one end of the retracting pin 49 and when the pivotal lever 85 is in its retracted position, shown in FIG. 10A, the leaf spring 95 is displaced outwardly by the pulling force in the direction of arrow 98 to permit free movement of the retracting pin. As soon as the upper frame assembly is tilted upwardly, this retention force is release by the pivoting of the lever 86, as above described, and the restoring force of the spring 95 causes the spring to assume its normal shape thereby moving the hole 97 into a pin receiving position, as shown in FIG. 10B, to immobilize the pin and prevent further retraction of the plunger bolt 46. Accordingly, when the patient support platform is tilted, it is not possible to disengage the bolts from the patient support frame. As soon as the upper frame assembly is restored to its horizontal position, the lever is pushed inside its lever housing 85, pulling on the leaf spring 95 and disengaging it from the pin 49.

As shown in FIG. 9C, a microswitch 47' has a switch arm (not shown) positioned to be actuated with the displacement of the bolt 46 whereby to disengage the operation of the pivoting system of the upper support frame. One microswitch is provided with each restraining side frame 35 and both must be engaged for the pivoting system to operate.

As shown in FIG. 7A, a shock absorbing pad 101, herein shown in phantom lines, is secured to the top wall 35" of the restraining side frames 35 and 35" whereby, to provide a restraining edge for the patient, and also to provide shock absorption when the restraining side frame is at its disengage vertical position. When at its disengage position, the absorbing pad will abut against any side frames of other structures, when the stretcher 10 is brought in abutting relation thereto. For example, if it is necessary to slide the patient support platform 11 laterally of the upper support frame, to position the patient support platform on another table to transfer the patient, it is only necessary to adjust the height of the patient support platform by means of the patient support cylinders to align the platform with a further support surface with the restraining side frame at its disengage position. The patient support platform can then be slid laterally of the upper support platform in an effortless manner due to the ball bearing support thereof, and transfer the patient on another adjacent table or support structure. Although not shown, the casters 27 have locking mechanisms thereon to immobilize the stretcher.

Figure 13:
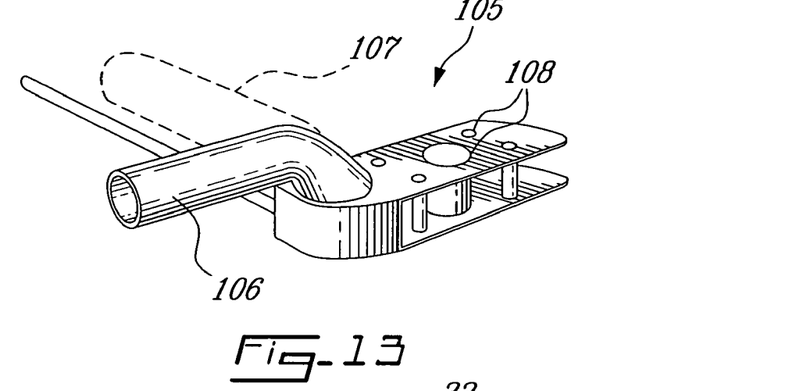
FIG. 13 is a perspective side view showing the construction of the attachment brackets and the support handles.

In order to provide support and ease of transportation of the patient support platform, there is provided, as shown in FIGS. 1 and 13, attachment brackets 105 in opposed corners of the patient support platform. These attachment brackets have a handle 106 pivotally connected thereto and hingeable to an extended position as shown in FIG. 13, and to a storage position as shown by phantom line 47. One or more connecting cavities 108 are also provided for attaching accessories thereto, such as the vertical support 109, shown in FIG. 1.

Figure 12A:
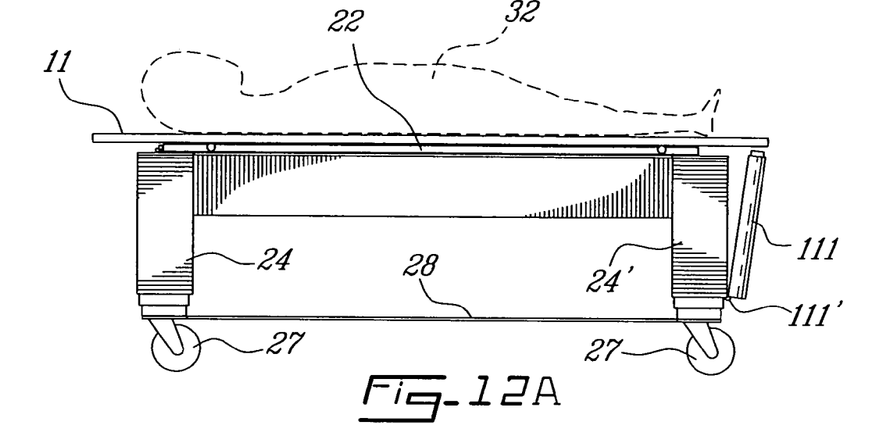
FIG. 12A is a side view of the pivoting cylinder which displaces the upper support platform to an angular position.
Figure 12B:
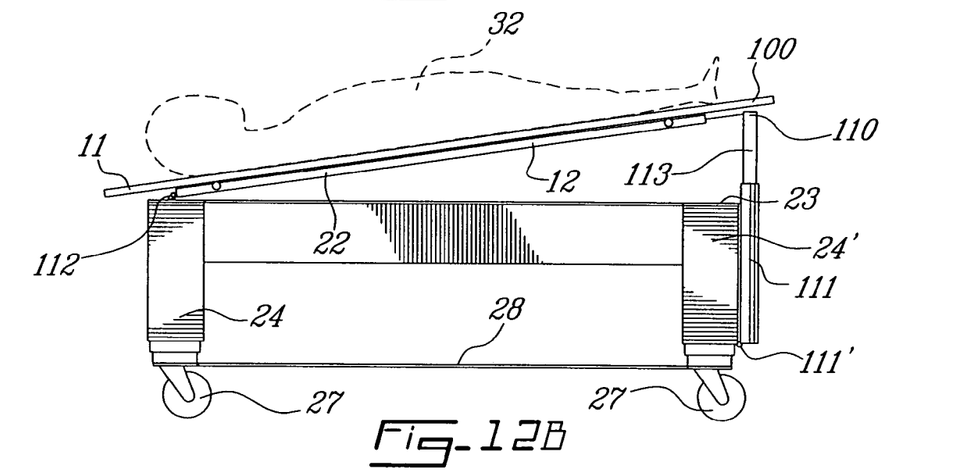
FIG. 12B illustrates the upper platform at an angular position with a patient thereon.
Figure 12C:
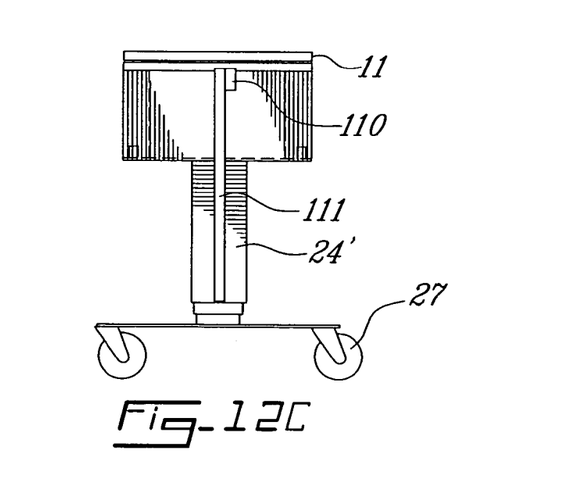
FIG. 12C is an end view of FIG. 12A.

With reference now to FIGS. 12A to 12C, there will be described the construction and operation of the upper support frame pivoting system to position the frame at an angle or at the Trendelenberg position. As herein shown, the elevating end 100 of the patient support platform support structure 12 is connected to a cylinder rod end 110 of an inclination cylinder 111. The cylinder 111 is pivoted at a lower end 111' thereof. The other transverse end of the lower rectangular support frame 22 is secured to a transverse hinge 112. When the inclination cylinder 111 is actuated, the cylinder rod 113 moves out of the cylinder 111 to position the patient 32 at a desired incline position. The piston rod 113 is actuated by an electric motor 110.

Figure 14:
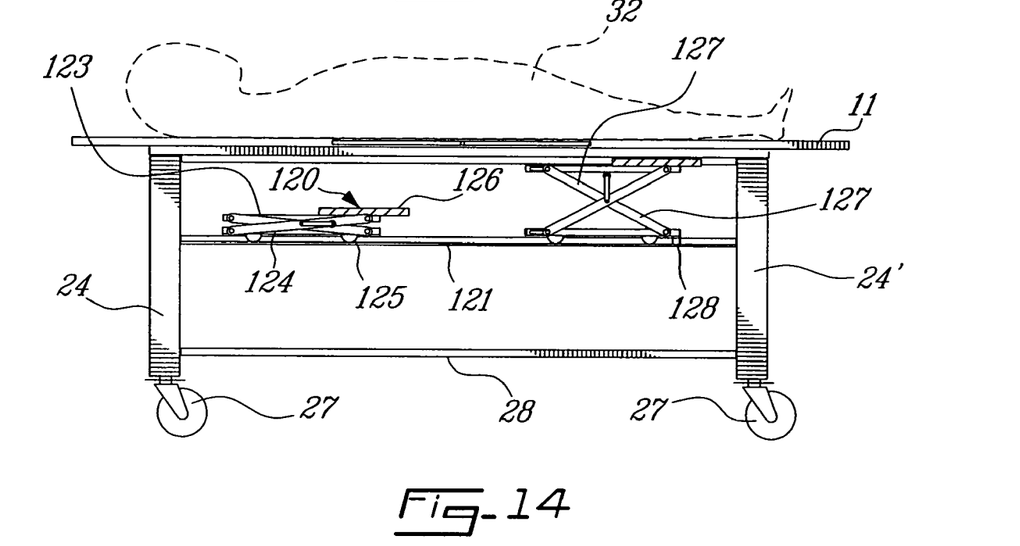
FIG. 14 is a side view illustrating the construction of the displaceable cassette support carriage positioned under the upper frame assembly.
Figure 15A:
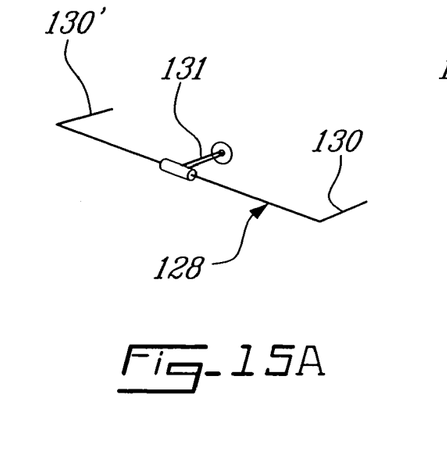
FIGS. 15A and 15B are perspective views showing the construction of the actuator to displace the scissor-link arms of the cassette support structure from a disengaged position, in FIG. 15A, to an engaged position, as shown in FIG. 15B.
Figure 15B:
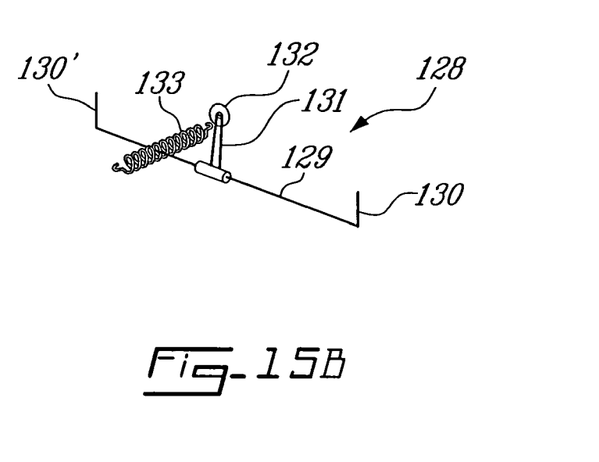

As previously described, the bearing support frame 13 and the lower rectangular support frame 22 are of a rectangular frame construction to provide a large opening under the patient support platform 11 to permit exposure of at least a major part of a patient's body lying on the patient support platform for the passage of imaging radiation through the patient's body. As shown in FIGS. 14 to 15B, a film cassette support carriage 120 is displaceable on a pair of support rails 121, secured in a lower end of the rectangular casing 9 and spaced under the upper support frame assembly and between the cylinders 24 and 24'. This carriage 120 is provided with a cassette attaching upper platform 123 which is displaceably secured to a lower platform 124 supported on wheels 125 whereby to displace the carriage 120 along the rails 121 to position a film cassette 126, sensitive to x-rays or other forms of radiation thereto, closely spaced under the platform 11. A displaceable linkage in the form of scissor link arms 127 interconnects the upper frame 123 to the lower frame 124 to position the cassette under the patient support platform within the large openings in the bearing support frame 13 and lower rectangular support frame 32.

The scissor link arms 127 are actuable to an elevated position of use where the cassette is close to the patient support platform, and to a lowered loading position where the carriage is collapsed whereby to provide visual and ease of access thereto, to load a cassette thereon, or to unload a cassette therefrom. The lower base 124 of the carriage may also be provided with a suitable locking means 128 to arrest the carriage at a desired position along the rails 121.

An actuator 128 is illustrated in FIGS. 15A and 15B whereby to displace the upper platform 123 of the carriage upwardly to a position of use, or downwardly to a loading or unloading position of the cassette.

This actuator may consist of various mechanisms, but as herein shown, it is comprised of a wire rod mechanism having a straight connecting rod portion 129 secured centrally of the scissor link arms 127. There is a pair of these link arms disposed along opposed edges of the carriage. A right angle projection at opposed ends of the rod constitutes an actuating arm 130' on opposed sides thereof. A central post 131, provided with a wheel 132 at an end thereof, is biased against a lower surface of the upper carriage frame 123. A spring 133 biases the arm 131 upwardly to a vertical position to actuate the scissor link arms. To disengage the link arms, the handle portions 130 are pivoted to a downward position as illustrated in FIG. 15A.

It is within the ambit of the present invention to cover any obvious modifications of the preferred embodiment described herein, provided such modifications fall within the scope of the appended claims.

The invention claimed is:

1. A stretcher with a dedicated multi-functional removable patient support platform said stretcher comprising a lower frame assembly supported on casters for displacing same on a support surface, an upper frame assembly supported elevated from said lower frame assembly, adjustable vertical supports adjustably interconnect said upper frame assembly to said lower frame assembly, means to extend and retract said adjustable vertical supports to adjust the height of said upper frame assembly relative to said lower frame assembly, said patient support platform being a rigid rectangular platform having a substantial portion thereof constructed of radiolucent material, detachable securement means for removably securing said patient support platform to a platform support structure of said upper frame assembly, said platform support structure having longitudinal axial restraining guide means to permit limited axial displacement of said patient support platform on said platform support structure, intermediate bearing means between said platform support structure and said patient support platform to permit effortless limited longitudinal displacement of said patient support platform on said platform support structure, said detachable securement means being displaceable from an engaged position to a disengaged position at which said patient support platform can be displaced laterally on said intermediate bearing means to permit said patient support platform to be transferred from said platform support structure laterally thereof in an effortless support manner.

2. A stretcher as claimed in claim 1 wherein said longitudinal axial restraining guide means comprises guide channels in opposed longitudinal edges of said patient support platform, and at least one restraining plunger bolt in opposed longitudinal restraining side frames projecting in respective ones of said channels for securing said patient support platform on said platform support structure and permitting said limited longitudinal displacement.

3. A stretcher as claimed in claim 2 wherein said detachable securement means is constituted by said restraining side frames being hinged restraining side frames for displaceably positioning a plunger bolt actuating mechanism to actuate said restraining plunger bolts associated with said opposed longitudinal restraining side frames, in and out of an associated one of said guide channels.

4. A stretcher as claimed in claim 3 wherein said hinged restraining side frames when in a plunger bolt disengaged position being located below a horizontal plane of said bearing means to provide unobstructed lateral displacement of said patient support platform on said bearing means.

5. A stretcher as claimed in claim 4 wherein each said hinged restraining side frames have an inserted u-shaped cross-section, a spring biased hinge in said u-shaped side frame to bias said hinged restraining side frame at said engaged position, and actuating means accessible from at least one end of said hinged restraining side frame to disengage said spring bias whereby said hinged restraining side frame may be displaced to said disengaged position, and retracting means for retracting said restraining plunger bolt from said channel to disengage said patient support platform from said platform support structure.

6. A stretcher as claimed in claim 5 wherein said actuating means is an axially pivotable rod to which is secured a hinge disengaging finger to trip said spring biased hinge to move to a hinge disengaged position.

7. A stretcher as claimed in claim 6 wherein a finger engaging lever is secured to a free end of said pivotal rod to cause axial rotational displacement of said rod to actuate said hinge disengaging finger.

8. A stretcher as claimed in claim 6 wherein there is further provided arresting means secured to said pivotal rod for obstructing engagement with an actuable locking element to immobilize said pivotal rod when said arresting means is actuated to prevent disengagement of said spring bias and maintain said hinge restraining side frame and said restraining plunger bolt engaged.

9. A stretcher as claimed in claim 4 wherein said plunger bolt is a spring actuated plunger bolt retained in a bolt housing secured to said restraining side frame, a cam pivotally secured to said housing and having a cam actuating edge, said cam having a bolt retracting arm connected to a retracting pin secured to said plunger bolt, bolt retracting means to retract said plunger bolt from said channel to permit said restraining side frame to pivot to a disengaged position.

10. A stretcher as claimed in claim 9 wherein said bolt retracting means is a finger engaging retracting flange secured to said plunger bolt to retract said bolt in said housing against a forwarding spring pressure of a bolt biasing coil spring.

11. A stretcher as claimed in claim 10 wherein said cam actuating edge engages a stationary wall portion of said platform support structure when said restraining side frame is at said disengaged position to maintain said plunger bolt retracted in said housing below said horizontal plane.

12. A stretcher as claimed in claim 9 wherein there is further provided bolt arresting means to maintain said plunger bolt extended from said housing and in a bolt head receiving cavity in a bottom wall of said channel to immovably secure said patient support platform to said platform support structure.

13. A stretcher as claimed in claim 12 wherein said bolt arresting means comprises an actuator secured to said platform support structure, and a retracting pin arrester displaceably connectable to said retracting pin, a cable interconnecting said actuator to said pin arrester whereby to cause said pin arrester to immobilize said retracting pin when said actuator senses upward displacement of said platform support structure when said platform support structure is tilted to maintain said patient support platform rigidly connected thereto.

14. A stretcher as claimed in claim 13 wherein said retracting pin arrester is a leaf spring capable of maintaining its shape and having an engaging end provided with a hole therein and aligned with said retracting pin, said spring engaging end being retracted from a free end of said pin by said cable, said cable being connected to a pivoted lever mounted in said actuator, said lever being biased against a horizontal support surface and exerting a pulling force on said leaf spring engaging end when said platform support structure is at a normal horizontal position, said pulling force being released when said platform support structure is lifted from said horizontal support surface causing said engaging end of said leaf spring to move toward said pin to cause said pin free and to project in said hole of said spring.

15. A stretcher as claimed in claim 5 wherein said hinged restraining side frame has a shock absorbing pad secured to a top wall thereof when said restraining side frame is at said engaged position, said shock absorbing pad being disposed to a side of said upper frame assembly when said hinged restraining side frame is at said plunger disengaged position to provide shock absorbing means.

16. A stretcher as claimed in claim 15 wherein said intermediate bearing means is constituted by longitudinal rows and transverse rows of restrained projecting ball bearings, said patient support platform having a flat lower surface supported for floating displacement on said ball bearings.

17. A stretcher as claimed in claim 16 wherein said upper frame assembly is provided with a rectangular bearing support frame defining opposed parallel arms and transverse parallel end arms, bearing retaining cavities in each said arms and providing for said ball bearing projecting from a top face of said arms.

18. A stretcher as claimed in claim 9 wherein said plunger has a bolt head biased within said channels to retain said patient support platform connected to said platform support structure while permitting said limited longitudinal displacement of said patient support platform on said intermediate bearing means.

19. A stretcher as claimed in claim 18 wherein said plunger bolt head has a sloped end head, said bolt head receiving cavity having a sloped top inner wall portion positioned for sliding frictional engagement with said sloped end head of said bolt whereby to secure said patient support platform in clamping engagement with said opposed restraining side frames and against said intermediate bearing means.

20. A stretcher as claimed in claim 18 wherein said adjustable supports are telescoping support cylinders, an electrical drive train to displace said cylinders and said patient support platform on said lower frame with said patient support platform immovably secured to said opposed restraining side frames by said lock means.

21. A stretcher as claimed in claim 3 wherein said guide channels are disposed in a central region of said opposed longitudinal edges of said patient support platform, said guide channels being restraining channels of a predetermined length to permit guided limited longitudinal displacement of said patient support platform a predetermined distance beyond opposed end edges of said platform support structure.

22. A stretcher as claimed in claim 21 wherein said predetermined distance is approximately 25% of the surface area of said patient support platform.

23. A stretcher as claimed in claim 2 wherein said patient support platform is provided with attachment brackets in opposed corners thereof, a handle secured to said attachment bracket, and one or more connecting cavities in said attachment brackets for connecting accessories thereto.

24. A stretcher as claimed in claim 17 wherein said rectangular bearing support frame has one of said transverse parallel end arms pivotally connected to a sub-frame immovably secured to a top end of said adjustable supports, an opposed one of said parallel end arms being secured to a cylinder rod end of a pivotally mounted inclination cylinder whereby to incline said patient support platform on said upper frame assembly with said patient support platform immovably secured to said sub-frame.

25. A stretcher as claimed in claim 24 wherein said plunger bolt is a spring actuated plunger bolt retained in a bolt housing secured to said restraining side frame, a cam pivotally secured to said housing and having a cam actuating edge, said cam having a bolt retracting arm connected to a retracting pin secured to said plunger bolt, bolt retracting means to retract said plunger bolt from said channel to permit said restraining side frame to pivot to a disengaged position.

26. A stretcher as claimed in claim 25 wherein said bolt retracting means is a finger engaging retracting flange secured to a rear end of said plunger bolt to retract manually said bolt in said housing against a forwarding spring pressure of a bolt biasing coil spring.

27. A stretcher as claimed in claim 2 wherein said upper frame assembly is a rectangular frame assembly constructed of peripheral side and end structural arms defining an open area therebetween dimensioned to permit exposure of at least part of a patient body lying on said patient support platform, for the passage of imaging radiation through said at least part of said patient body, through said radiolucent material of said patient platform and onto a film cassette adjustably supported under said upper frame assembly on a pair of horizontal support rails; a carriage displaceable on said support rails along the longitudinal axis of said patient support platform, said carriage having a cassette attachment platform supported on a displaceable linkage to displace said cassette attachment platform from a retracted loading position away from patient support platform to a position of use closely spaced under said patient support platform.

28. A stretcher as claimed in claim 27 wherein said displaceable linkages are scissor link arms interconnecting said cassette attachment platform to a carriage base supported on said rails by wheels, and an actuator to displace said scissor link arms and engage them at said position of use.

29. A stretcher as claimed in claim 28 wherein said carriage base is provided with arresting means to arrest same at a desired position along said rails.

30. A stretcher as claimed in claim 8 wherein said actuable locking element is an arresting pin displaceable to a projected position in said hinged restraining side frame when said platform support structure is immediately actuated to pivot, and means to retract said arresting finger from said hinged restraining side frame.

31. A stretcher as claimed in claim 30 wherein said arresting pin is actuated by a mechanical sensor which is spring biased to sense the pivotal displacement of the platform support structure.

* * * * *